US010583034B2

(12) United States Patent
Chin et al.

(10) Patent No.: US 10,583,034 B2
(45) Date of Patent: Mar. 10, 2020

(54) HYDROPHILIC POLYMER COATINGS WITH DURABLE LUBRICITY AND COMPOSITIONS AND METHODS THEREOF

(71) Applicant: HydroGlyde Coatings LLC, Brookline, MA (US)

(72) Inventors: Stacy Lee Chin, Brookline, MA (US); Benjamin Goldman Cooper, Lynnfield, MA (US); Ruiqing Xiao, Boston, MA (US); Mark W. Grinstaff, Brookline, MA (US)

(73) Assignee: HydroGlyde Coatings LLC, Brookline, MA (US)

(*) Notice: Subject to any disclaimer, the term of this patent is extended or adjusted under 35 U.S.C. 154(b) by 0 days.

(21) Appl. No.: 16/585,592

(22) Filed: Sep. 27, 2019

(65) Prior Publication Data

US 2020/0038233 A1 Feb. 6, 2020

Related U.S. Application Data

(60) Division of application No. 16/267,872, filed on Feb. 5, 2019, now Pat. No. 10,449,084, which is a continuation of application No. PCT/US2017/051783, filed on Sep. 15, 2017.

(60) Provisional application No. 62/408,625, filed on Oct. 14, 2016.

(51) Int. Cl.
| | |
|---|---|
| *C08L 7/02* | (2006.01) |
| *A61F 6/04* | (2006.01) |
| *B32B 27/36* | (2006.01) |
| *B32B 27/30* | (2006.01) |
| *B32B 27/28* | (2006.01) |
| *C08L 9/08* | (2006.01) |
| *C09D 107/02* | (2006.01) |
| *C09D 109/08* | (2006.01) |
| *B32B 27/26* | (2006.01) |
| *C08J 7/04* | (2020.01) |
| *C08L 11/02* | (2006.01) |
| *C08L 29/04* | (2006.01) |

(52) U.S. Cl.
CPC ............ *A61F 6/04* (2013.01); *B32B 27/26* (2013.01); *B32B 27/28* (2013.01); *B32B 27/285* (2013.01); *B32B 27/30* (2013.01); *B32B 27/302* (2013.01); *B32B 27/306* (2013.01); *B32B 27/36* (2013.01); *C08J 7/042* (2013.01); *C08L 7/02* (2013.01); *C08L 9/08* (2013.01); *C08L 11/02* (2013.01); *C09D 107/02* (2013.01); *C09D 109/08* (2013.01); *B32B 2307/728* (2013.01); *C08J 2300/26* (2013.01); *C08J 2307/00* (2013.01); *C08J 2307/02* (2013.01); *C08J 2347/00* (2013.01); *C08J 2407/02* (2013.01); *C08J 2409/02* (2013.01); *C08L 29/04* (2013.01)

(58) Field of Classification Search
CPC ............... C08L 7/02; C08L 9/08; C08L 11/02
See application file for complete search history.

(56) References Cited

U.S. PATENT DOCUMENTS

| | | | |
|---|---|---|---|
| 4,119,094 A | 10/1978 | Micklus et al. | |
| 4,412,017 A | 10/1983 | Van Eenam | |
| 4,499,154 A | 2/1985 | Podell | |
| 5,688,855 A | 11/1997 | Stoy et al. | |
| 6,365,278 B1 | 4/2002 | Hutchinson | |
| 7,405,186 B2 | 7/2008 | Harrison | |
| 8,062,722 B2 | 11/2011 | Blum et al. | |
| 8,770,201 B2 | 7/2014 | Zedalis et al. | |
| 2005/0043474 A1* | 2/2005 | Schmidt | A61L 15/60 524/556 |
| 2014/0326250 A1 | 11/2014 | Arnold | |
| 2016/0145401 A1* | 5/2016 | Potter | C08J 5/02 427/372.2 |

FOREIGN PATENT DOCUMENTS

| | | |
|---|---|---|
| EP | 0860172 B1 | 6/2003 |
| EP | 2349142 B1 | 1/2015 |
| EP | 2305744 B1 | 8/2016 |
| WO | 2006/105001 A2 | 10/2006 |

OTHER PUBLICATIONS

PCT/US2017/051783, Int'l Search Report and Written Opinion of the ISA, dated Jan. 11, 2018.
Klamklang, et al. (2002) "Preparation and Characterization of Hydrophilic Pervaporation Membranes from Natural Rubber Latex Based Polymer" ScienceAsia 28:135-143.
Rouilly, et al. (2004) "Synthesis and Properties of Composites of Starch and Chemically Modified Natural Rubber" Polymer 45:7813-7820.
Yu, et al. (2006) "Polymer Blends and Composites from Renewable Resources" Prog. Polym. Sci. 31:576-602.
Vieira, et al. (2011) "Natural-based Plasticizers and Biopolymer Films: A Review" European Polymer Journal 47:254-263.
Nakason, et al. (2013) "Synthesis and Characterization of Water Swellable Natural Rubber Vulcanizates" European Polymer Journal 49:1098-1110.

\* cited by examiner

*Primary Examiner* — Peter D. Mulcahy
(74) *Attorney, Agent, or Firm* — Milstein Zhang & Wu LLC

(57) ABSTRACT

The invention provides a novel hydrophilic polymer and latex polymer blend coating formulation and compositions thereof, and their use on various devices (e.g., prophylactic and medical devices) to form hydrophilic and flexible coatings with durable lubricity.

18 Claims, 4 Drawing Sheets

US 10,583,034 B2

HYDROPHILIC POLYMER COATINGS WITH DURABLE LUBRICITY AND COMPOSITIONS AND METHODS THEREOF

PRIORITY CLAIMS AND RELATED PATENT APPLICATIONS

This application is a divisional of and claims the benefit of priority to U.S. patent application Ser. No. 16/267,872, filed Feb. 5, 2019, which claims the benefit of priority to PCT/US2017/051783, filed Sep. 15, 2017, which claims the benefit of priority to U.S. Provisional Application Ser. No. 62/408,625, filed on Oct. 14, 2016, the entire content of each of which is incorporated herein by reference in its entirety.

STATEMENT REGARDING FEDERALLY FUNDED RESEARCH OR DEVELOPMENT

This invention was made with government support under Grant No. R43HD089856-01A1 awarded by the Eunice Kennedy Shiver Nation Institute of Child Health and Human Development Center of the U.S. National Institute of Health. The Government has certain rights in the invention.

TECHNICAL FIELD OF THE INVENTION

The invention generally relates to polymer formulations and use thereof in surface coatings of various products. More particularly, the invention relates to a novel hydrophilic polymer and latex polymer blend coating formulation and compositions thereof, and their use on various devices (e.g., prophylactic and medical devices) to form hydrophilic and flexible coatings with durable lubricity.

BACKGROUND OF THE INVENTION

Natural or synthetic latex possesses favorable physical and rheological properties due to its soft elastic characteristics and high resistance to mechanical stresses and heat. Because of these desirable properties, latex is widely incorporated in a number of consumer goods and medical devices (e.g., condoms). Due to its hydrophobicity, however, latex is not compatible with blood, and can irreversibly adsorb proteins and platelets on its surface when in contact with biologics. Additionally, high frictional and abrasive forces can occur between the interface of latex-based medical devices and tissues, leading to discomfort, increased risks of infections, tissue damage, and pain for the user.

According to the World Health Organization, the lack of adequate lubrication remains a major drawback for proper and consistent condom use. The minimal amount of lubrication included with condoms during packaging is typically insufficient to maintain the condom's lubricity throughout intercourse. Consequently, partners will either (1) not use a condom and increase risks for unwanted pregnancies and spread of Sexually transmitted infections (STIs), or (2) use an inadequately lubricious condom resulting in mucosal microtrauma, pain, and decreased satisfaction between partners. This microtrauma and pain may arise from dramatically increased penetrative force during intercourse when lubrication is inadequate. Typical healthy vaginal lubrication has been reported to require a penetrative force of 0.5 kg, whereas a typical post-menopausal or poor vaginal lubrication requires a three-fold greater penetrative force of 1.5 kg. There is also a significant demand for better lubrication products and strategies to be used with condoms, particularly for older women in menopause and post-menopausal stages affected by vaginal dryness.

Silicone-based lubricants are the most commonly used lubricants today and are applied to both male and female condoms during the manufacturing process prior to packaging. Despite this, condom consumer satisfaction with condom lubricity remains low. Unfortunately, these unmet needs exacerbate the societal stigma and negative perception that condoms are uncomfortable and will decrease pleasure during intercourse, which adversely affects the consistency of proper condom usage.

A variety of methods have been explored to chemically or physically modify natural or synthetic latex to possess hydrophilic and lubricous properties, all with limited success. The different types of hydrophilic monomers that are compatible for polymerization reactions are currently limited. Surface modification strategies involving the application of hydrophilic coatings to the surface of latex-based substrates have proven to be challenging, for example, due to persistent delamination between the coating and latex.

Thus, there is an ongoing critical need to develop novel durable, flexible, non-toxic and low-costing hydrophilic coatings and application strategies that are compatible with natural and synthetic latex-based surfaces and medical devices, particularly for condoms.

SUMMARY OF THE INVENTION

The invention is based in part on the unexpected discovery of a novel hydrophilic polymer and latex polymer blend coating formulation, and compositions thereof, that are suitable for use on various devices (e.g., condoms and other prophylactic or medical devices) to form hydrophilic and flexible coatings with durable lubricity.

A key feature of the invention is that, when in contact with water or an aqueous solution, the hydrophilic coating becomes slippery with durable lubricity, resulting in lowered frictional forces when in contact with tissue or other interfaces. This thin hydrophilic coating is able to maintain its lubricity continuously when in contact with surfaces in the presence of water without impacting on the mechanical and physical properties of the coated device.

In one aspect, the invention generally relates to an aqueous composition, which comprises: a hydrophilic polymer; a suspension of latex polymer microparticles; and, optionally, one or more of vulcanizing or accelerating agents. The hydrophilic polymer has a mean molecular weight in the range from about 1 kDa to about 10,000 kDa and is present in the composition at a concentration from about 2 w/v % to about 10 w/v %. The latex polymer microparticles are present in the composition at a concentration from about 20 w/v % to about 60 w/v %. The weight ratio of the hydrophilic polymer to the latex polymer microparticles is in the range from about 1:1 to about 10:1.

In another aspect, the invention generally relates to a composition formed by mixing: a first aqueous solution of a hydrophilic polymer with a concentration in the range from about 1 w/v % to about 20 w/v %; and a second aqueous suspension of latex polymer microparticles with a concentration in the range from about 20 w/v % to about 65 w/v %. The hydrophilic polymer has a mean molecular weight in the range from about 1 kDa to about 1,000 kDa. The volume ratio of the first aqueous solution to the second aqueous suspension is in the range from about 1:1 to about 1:3.

In yet another aspect, the invention generally relates to a cured material formed by heating a composition disclosed herein for a time sufficient to form interpenetrating polymer networks of crosslinked hydrophilic polymer and latex polymer. The process results in the physical entrapment of the hydrophilic polymer on the latex surface upon the heat curing process. Interpenetrating polymer networks can reinforce and improve the properties of the resulting polymer matrix, This curing process can also include but is not limited to using chemical reagents to form the polymer network.

In yet another aspect, the invention generally relates to a latex condom. The latex condom includes: a sheath of an elastomeric material selected from natural or synthetic rubber latex, the sheath having an outer surface and an inner surface; and a layered coating comprising a first or base layer disposed on and adhered to at least a portion of the outer surface of the sheath and a second or top layer disposed on and adhered to at least a portion of the first or base layer. The first or base layer is a cured latex polymer. The second or top layer is a cured blend of a latex polymer and a hydrophilic polymer having a mean molecular weight in the range from about 1 kDa to about 1,000 kDa, wherein the weight ratio of the hydrophilic polymer to the latex polymer is in the range from about 10:1 to about 1:10.

In yet another aspect, the invention generally relates to a packaged condom product comprising one or more latex condoms disclosed herein.

In yet another aspect, the invention generally relates to a method for manufacturing a condom. The method includes: providing a sheath of an elastomeric material selected from natural or synthetic rubber latex, the sheath having an outer surface and an inner surface; depositing a first layer of an aqueous suspension of a latex polymer to at least a portion of the outer surface of the sheath; curing the latex polymer with exposure to heat for a time sufficient to form a first or base layer of cured latex polymer; depositing a second layer of a composition, comprising a hydrophilic polymer and a suspension of latex polymer, to at least a portion of the first or base layer; and curing the second layer of hydrophilic polymer and latex polymer with exposure to heat for a time sufficient to form a second or top layer. The hydrophilic polymer has a mean molecular weight in the range from about 1 kDa to about 1,000 kDa and is present in the composition at a concentration from about 2 w/v % to about 10 w/v %. The latex polymer microparticles are present in the composition at a concentration from about 20 w/v % to about 65 w/v %. The weight ratio of the hydrophilic polymer to the latex polymer microparticles is in the range from about 1:1 to about 10:1.

In yet another aspect, the invention generally relates to a condom manufactured by a method disclosed herein.

DEFINITIONS

Figure 1:
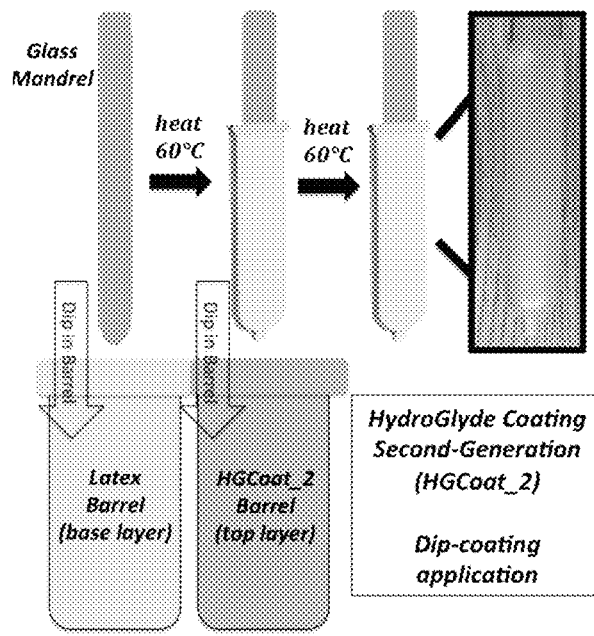
FIG. 1. Coating application onto condoms using a dip-coating approach. A glass mandrel is dipped into a latex barrel to form the first or base layer that is cured with heat. This is followed by a second dip into the hydrophilic and latex polymer blend barrel and is followed by heat to cure onto the base layer to from the coated condoms.

Unless stated otherwise, or implicit from context, the following terms and phrases include the meanings provided below. The definitions are provided to aid in describing particular embodiments, and are not intended to limit the claimed invention, because the scope of the invention is limited only by the claims. Further, unless otherwise required by context, singular terms shall include pluralities and plural terms shall include the singular. Thus, as used herein and in the claims, the singular forms include the plural reference and vice versa unless the context clearly indicates otherwise.

Other than in the operating examples, or where otherwise indicated, all numbers expressing quantities of ingredients or reaction conditions used herein should be understood as modified in all instances by the term "about." The term "about" when used in connection with a value can mean 5% of the value being referred to. For example, about 100 means from 95 to 105.

As used herein, the term "latex" refers to natural or synthetic latex, which include vulcanized or non-vulcanized. The term "latex polymer" refers to the polymer(s) the latex is formed from. Typically, the latex substrate is hydrophobic. In some embodiments, the latex is biocompatible provided that the user does not have an adverse or allergic reaction when in contact with latex. Synthetic latex may include synthetic rubber materials, including but not limited to nitrile, hydrogenated nitrile, ethylene-propylene, fluorocarbon, chloroprene, silicone, fluorosilicone, polyacrylate, ethylene acrylic, acrylic polymers, styrenebutadiene, acrylonitrile butadiene, polyvinyl acetate, or polyurethane rubbers.

As used herein, the term "hydrophilic polymer" refers to homo- or co-polymers that exhibit hydrophilic properties, i.e., having a strong affinity for water. Non-limiting examples of hydrophilic polymers include poly(vinyl pyrrolidone) (PVP), poly(ethylene glycol) (PEG), poly(vinyl alcohol) (PVA), poly(N-isopropylacrylamide), polyacrylamide, poly(2-oxazoline), polyethylenimine, polyacrylic acid), polymethacrylate, poly(2-ethylacrylic acid), poly(acrylic acid), poly(sulfopropyl acrylate) potassium salt, poly(2- methacryloyloxyethyl phosphorylchlorine), poly(2-propylacrylic acid), poly(methacrylic acid), poly(2-hydroxypropyl methacrylate), hydroxypropylmethylcellulose (HPMC), poly(oxanorbornene), polyelectrolytes, and co-polymers thereof.

As used herein, the term "hydrophilic latex blend" or "hydrophilic and latex polymer blend" refers to an evenly-mixed and viscous solution mixture composed of a hydrophilic polymer and latex dissolved in an aqueous solution.

As used herein, the term "non-cytotoxic" refers to biocompatibility with mammalian cells.

As used herein, the term "biocompatible" refers to the absence of an adverse acute, chronic or escalating biological response to an implant or coating, and is distinguished from a mild, transient inflammation which typically accompanies surgery or implantation of foreign objects into a living organism.

As used herein, the term "viscous" means a liquid material, e.g., a solution having viscosity of several hundreds centipoises to several millions centipoises. For example the measurement of viscosity can range from about $10^2$ cP to about $10^7$ cP.

DETAILED DESCRIPTION OF THE INVENTION

The invention provides a novel hydrophilic polymer and latex polymer blend coating formulation and compositions thereof. These compositions are suitable for use, for example, as hydrophilic coating on various devices, such as condoms and other prophylactic or medical devices, to form hydrophilic and flexible coatings with durable lubricity. When in contact with water or an aqueous solution, the hydrophilic coating becomes durably lubricious. This thin hydrophilic coating is able to maintain its lubricity continuously when in contact with surfaces in the presence of water without impacting on the mechanical and physical properties of the coated device. Thus, frictional forces are lowered when in contact with tissue or other interfaces. A durable and lubricious hydrophilic coating on latex condoms can lead to a reduction of condom breakage, pain, discomfort, and mucosal microtrauma for the user. Other devices that can benefit from such a coating include, for example, solid, non-flexible and flexible surfaces of prophylactic and biomedical latex-based devices or tools.

The hydrophilic and latex polymer blend coating formulation includes two main components in an aqueous environment: a hydrophilic polymer (e.g., poly(vinyl pyrrolidone) (PVP), poly(ethylene glycol) (PEG), or poly(vinyl alcohol) (PVA), and a natural or synthetic latex suspension (e.g., having a similar composition as the substrate to be coated). These two components are present at a pre-selected ratio and mixed so as to generate a well-mixed and viscous solution (a liquid suspension). In a typical coating application, for example to a latex condom, a thin and even layer of the latex blend coating formulation is applied to the surface of latex condoms (either after a base layer is formed or directly on the latex condom) via dip-coating, followed by immediate exposure to heat to evaporate the solvent and form a cured coating.

As is disclosed herein for the first time, the hydrophilic coatings of the invention afford: (1) reduced frictional forces at the latex and tissue interfaces, (2) reduced risk of device breakage and infections associated with long-term latex exposure to skin and tissue, (3) improved biocompatibility of latex through imparting a non-fouling surface, and (4) improved user satisfaction, comfort, and safety associated with latex devices.

In one aspect, the invention generally relates to an aqueous composition, which comprises: a hydrophilic polymer; a suspension of latex polymer microparticles; and, optionally, one or more of vulcanizing or accelerating agents. The hydrophilic polymer has a mean molecular weight in the range from about 1 kDa to about 10,000 kDa and is present in the composition at a concentration from about 2 w/v % to about 10 w/v %. The latex polymer microparticles are present in the composition at a concentration from about 20 w/v % to about 60 w/v %. The weight ratio of the hydrophilic polymer to the latex polymer microparticles is in the range from about 1:1 to about 10:1.

Any suitable hydrophilic polymer may be employed. In certain embodiments, the hydrophilic polymer comprises one or more hydrophilic polymers selected from the group consisting of: homo- or co-polymers of vinyl pyrrolidone, ethylene glycol, and/or vinyl alcohol. In certain embodiments, the hydrophilic polymer comprises a second hydrophilic polymer.

In certain embodiments, the hydrophilic polymer comprises one of poly(vinyl pyrrolidone) (PVP), poly(ethylene glycol) (PEG), and poly(vinyl alcohol) (PVA). In certain embodiments, the hydrophilic polymer comprises PVP.

The hydrophilic polymer may have any suitable molecular weight, for example, having a mean molecular weight in the range from about 1 kDa to about 10,000 kDa (e.g., from about 1 kDa to about 5,000 kDa, from about 1 kDa to about 1,000 kDa, from about 1 kDa to about 500 kDa, from about 1 kDa to about 100 kDa, from about 1 kDa to about 50 kDa, from about 1 kDa to about 10 kDa, from about 5 kDa to about 10,000 kDa, from about 10 kDa to about 10,000 kDa, from about 50 kDa to about 10,000 kDa, from about 100 kDa to about 10,000 kDa, from about 500 kDa to about 10,000 kDa, from about 1,000 kDa to about 10,000 kDa, from about 5,000 kDa to about 10,000 kDa, from about 10 kDa to about 5,000 kDa, from about 50 kDa to about 1,000 kDa, from about 100 kDa to about 500 kDa).

In certain embodiments, the hydrophilic polymer has a mean molecular weight in the range from about 1 kDa to about 1,000 kDa (e.g., from about 1 kDa to about 50 kDa, from about 50 kDa to about 500 kDa, from about 500 kDa to about 1,000 kDa).

In certain embodiments, the hydrophilic polymer has a mean molecular weight in the range from about 1 kDa to about 100 kDa (e.g., from about 1 kDa to about 10 kDa, from about 10 kDa to about 50 kDa, from about 50 kDa to about 100 kDa).

The hydrophilic polymer may be present in the composition at any suitable concentration in aqueous composition, for example, from about 2 w/v % to about 10 w/v % (e.g., from about 2 w/v % to about 9 w/v %, from about 2 w/v % to about 8 w/v %, from about 2 w/v % to about 7 w/v %, from about 2 w/v % to about 6 w/v %, from about 2 w/v % to about 5 w/v %, from about 3 w/v % to about 10 w/v %, from about 4 w/v % to about 10 w/v %, from about 5 w/v % to about 10 w/v %, from about 6 w/v % to about 10 w/v %, from about 3 w/v % to about 8 w/v %, from about 4 w/v % to about 9 w/v %,).

In certain embodiments, the hydrophilic polymer is present in the composition at a concentration from about 2 w/v % to about 7 w/v % (e.g., from about 2 w/v % to about 3.5 w/v %, from about 3.5 w/v % to about 5 w/v %, from about 5 w/v % to about 7 w/v %).

The latex polymer microparticles may be natural latex or synthetic latex. Synthetic rubber latex may be synthetized from, for example, nitrile, butadiene, styrene-butadiene, chloroprene, isobutylene, or co-polymers thereof.

The latex polymer microparticles may be present in the composition at any suitable concentration in aqueous composition, for example, from about 20 w/v % to about 65 w/v % (e.g., from about 30 w/v% to about 65 w/v %, from about 40 w/v% to about 65 w/v %, from about 50 w/v % to about 65 w/v %, from about 20 w/v % to about 50 w/v %, from about 20 w/v % to about 40 w/v %, from about 20 w/v % to about 30 w/v %).

In certain embodiments, the latex polymer microparticles is present in the composition at a concentration from about 35 w/v % to about 55 w/v % (e.g., from about 35 w/v % to about 40 w/v %, from about 40 w/v % to about 45 w/v %, from about 45 w/v % to about 50 w/v %, from about 50 w/v % to about 55 w/v %).

The weight ratio of the hydrophilic polymer to the latex polymer microparticles in aqueous composition may be any suitable value, for example, in the range from about 1:1 to about 1:3 (e.g., about 1:1 to about 1:2.5, about 1:1 to about 1:2, about 1:1 to about 1:1.5, about 1:1.5 to about 1:3, about 1:2 to about 1:3, about 1:2.5 to about 1:3).

The aqueous composition is preferably a well-mixed and stable suspension.

The aqueous composition is preferably a viscous aqueous composition, for example, with a viscosity in the range from about 10 cP to about $10^{10}$ cP (e.g., from about 10 cP to about $10^2$ cP, from about 10 cP to about $10^4$ cP, from about 10 cP to about $10^6$ cP, from about 10 cP to about $10^8$ cP, from about $10^2$ cP to about $10^{10}$ cP, from about $10^4$ cP to about $10^{10}$ cP, from about $10^6$ cP to about $10^{10}$ cP, from about $10^8$ cP to about $10^{10}$ cP, from about $10^2$ cP to about $10^6$ cP, from about $10^4$ cP to about $10^8$ cP).

The compositions disclosed herein may further include additives that impact chemical and/or physical properties of the composition, such as vulcanizing and/or accelerating agents. Any suitable vulcanizing agents (e.g., diisopropyl xanthogen polysulfide, sulfur, or ammonia) may be used. Any suitable accelerating agents (e.g., zinc-N-diethyl-dithio-carbomate, zinc-N-dibutyl-dithio-carbomate, or ammonia) may be used.

The compositions disclosed herein may further include one or more of antimicrobials, antifungals, antivirals, vitamins, colors, and antibiotics.

In another aspect, the invention generally relates to a composition formed by mixing: a first aqueous solution of a hydrophilic polymer with a concentration in the range from about 1 w/v % to about 20 w/v %; and a second aqueous suspension of latex polymer microparticles with a concentration in the range from about 20 w/v % to about 65 w/v %. The hydrophilic polymer has a mean molecular weight in the range from about 1 kDa to about 1,000 kDa. The volume ratio of the first aqueous solution to the second aqueous suspension is in the range from about 1:1 to about 1:3.

In certain embodiments, the hydrophilic polymer at a concentration in the composition from about 2 w/v % to about 7 w/v % (e.g., from about 2 w/v % to about 3.5 w/v %, from about 3.5 w/v % to about 5 w/v %, from about 5 w/v % to about 7 w/v %) and the latex polymer microparticles at a concentration from about 20 w/v % to about 65 w/v % (e.g., e.g., from about 30 w/v % to about 65 w/v %, from about 40 w/v % to about 65 w/v %, from about 50 w/v % to about 65 w/v %, from about 20 w/v % to about 50 w/v %, from about 20 w/v % to about 40 w/v %, from about 20 w/v % to about 30 w/v %).

In certain embodiments, the composition includes one or more of vulcanizing agents. In certain embodiments, the composition includes one or more of accelerating agents.

In certain embodiments, one or more of vulcanizing agents or the one or more of accelerating agents are present in the first aqueous solution a hydrophilic polymer.

In certain embodiments, one or more of vulcanizing agents or the one or more of accelerating agents are present in the second aqueous suspension of latex polymer microparticles.

In certain embodiments, the vulcanizing agents are selected from the group consisting of: diisopropyl xanthogen polysulfide, sulfur and ammonia.

In certain embodiments, the accelerating agents are selected from the group consisting of: zinc-N-diethyl-dithio-carbomate, zinc-N-dibutyl-dithio-carbomate and ammonia.

In certain embodiments, one or more of antimicrobials, antifungals, antivirals, vitamins, colors, or antibiotics may be present in the first aqueous solution a hydrophilic polymer.

In certain embodiments, one or more of antimicrobials, antifungals, antivirals, vitamins, colors, or antibiotics may be present in the second aqueous suspension of latex polymer microparticles.

In yet another aspect, the invention generally relates to a cured material formed by heating a composition disclosed herein for a time sufficient to form interpenetrating polymer networks of crosslinked hydrophilic polymer and latex polymer.

In certain embodiments, the material is a coating forming a surface of a product. In certain embodiments, the material is a coating forming a partial surface of a product. In certain embodiments, the material is a coating forming a complete surface of a product.

The cured material may be used with any suitable product, for example, selected from the group consisting: a condom, a sex toy, a surgical device, a medical implant, or a glove.

In certain embodiments, the cured material is less toxic than the uncured coated material.

In yet another aspect, the invention generally relates to a latex condom. The latex condom includes: a sheath of an elastomeric material selected from natural or synthetic rubber latex, the sheath having an outer surface and an inner surface; and a layered coating comprising a first or base layer disposed on and adhered to at least a portion of the outer surface of the sheath and a second or top layer disposed on and adhered to at least a portion of the first or base layer. The first or base layer is a cured latex polymer. The second or top layer is a cured blend of a latex polymer and a hydrophilic polymer having a mean molecular weight in the range from about 1 kDa to about 1,000 Da, wherein the weight ratio of the hydrophilic polymer to the latex polymer is in the range from about 10:1 to about 1:10.

In certain embodiments, the layered coating includes a third or top layer disposed on and adhered to the second layer, wherein the third or top layer is a cured blend of latex polymer and a hydrophilic polymer having a mean molecular weight in the range from about 1 kDa to about 1,000 kDa, wherein the weight ratio of the hydrophilic polymer to the latex polymer is in the range from about 1:1 to about 10:1.

In certain embodiments, the layered coating comprising a further or top layer disposed on and adhered to the third layer, wherein the further or top layer is a cured blend of latex polymer and a hydrophilic polymer having a mean molecular weight in the range from about 1 kDa to about 1,000 kDa, wherein the weight ratio of the hydrophilic polymer to the latex polymer is in the range from about 1:1 to about 10:1.

In certain embodiments, the first layer covers substantially the entire outer surface of the latex condom, the second layer covers substantially all of the first layer, and, if present, the third layer covers substantially all of the second layer surface, and so forth, respectively.

In certain embodiments, the elastomeric material is selected from natural or synthetic rubber latex. In certain embodiments, the synthetic rubber latex is synthetized from nitrile, butadiene, styrene-butadiene, chloroprene, isobutylene, or co-polymers thereof.

In certain embodiments, the weight ratio of the hydrophilic polymer to the latex polymer is in the range from about 1:1 to about 10:1 (e.g., from about 1:1 to about 7:1, from about 1:1 to about 5:1, from about 1:1 to about 3:1, from about 3:1 to about 10:1, from about 5:1 to about 10:1, from about 7:1 to about 10:1).

In certain embodiments, the weight ratio of the hydrophilic polymer to the latex polymer is in the range from about 1:1 to about 5:1 (e.g., from about 1:1 to about 3:1, from about 1:1 to about 3:1, from about 5:1 to about 5:1, from about 3:1 to about 5:1).

In certain embodiments, the hydrophilic polymer comprises one of poly(vinyl pyrrolidone) (PVP), poly(ethylene glycol) (PEG), and poly(vinyl alcohol) (PVA). In certain embodiments, the hydrophilic polymer comprises PVP.

In certain embodiments, the hydrophilic polymer comprises a second hydrophilic polymer.

In certain embodiments, the latex condom further includes a silicon-based or water-based lubricant applied to the top layer.

In certain embodiments, the latex condom further includes a coating of powders or dusting agents, selected from cornstarch, baby powder, or talc, applied to the top layer.

In certain embodiments, when the latex condom contacts with moisture or water, the top layer becomes slippery with durable lubricity.

In yet another aspect, the invention generally relates to a packaged condom product comprising one or more latex condoms disclosed herein.

In yet another aspect, the invention generally relates to a method for manufacturing a condom. The method includes: providing a sheath of an elastomeric material selected from natural or synthetic rubber latex, the sheath having an outer surface and an inner surface; depositing a first layer of an aqueous suspension of a latex polymer to at least a portion of the outer surface of the sheath; curing the latex polymer with exposure to heat for a time sufficient to form a first or base layer of cured latex polymer; depositing a second layer of a composition, comprising a hydrophilic polymer and a suspension of latex polymer, to at least a portion of the first or base layer; and curing the second layer of hydrophilic polymer and latex polymer with exposure to heat for a time sufficient to form a second or top layer. The hydrophilic polymer has a mean molecular weight in the range from about 1 kDa to about 1,000 kDa and is present in the composition at a concentration from about 2 w/v % to about 10 w/v %. The latex polymer microparticles are present in the composition at a concentration from about 20 w/v % to about 65 w/v %. The weight ratio of the hydrophilic polymer to the latex polymer microparticles is in the range from about 1:1 to about 10:1.

In certain embodiments, the method further includes: depositing a third or top layer of a composition, comprising a hydrophilic polymer and a suspension of latex polymer, to at least a portion of the second layer; and curing the third layer of hydrophilic polymer and latex polymer with exposure to heat for a time sufficient to form a third or top layer.

In certain embodiments, the first layer covers substantially all of the outer surface of the latex condom, the second layer covers substantially all of the first layer, and, if present, the third layer covers substantially all of the second layer surface, and so forth, respectively.

In certain embodiments, curing the latex polymer is conducted at a temperature between about 25° C. to about 70° C. (e.g., between about 35° C. to about 70° C., about 40° C. to about 70° C., about 50° C. to about 70° C., about 60° C. to about 70° C., about 25° C. to about 60° C., about 25° C. to about 50° C., about 25° C. to about 40° C., about 30° C. to about 60° C.) for a time period from about 5 to about 60 minutes (e.g., from about 5 to about 45 minutes, from about 5 to about 30 minutes, from about 5 to about 15 minutes, from about 5 to about 10 minutes, from about 10 to about 30 minutes, from about 15 to about 30 minutes, from about 20 to about 30 minutes, from about 10 to about 25 minutes, from about 10 to about 20 minutes).

In certain embodiments, curing the hydrophilic polymer and a suspension of latex polymer is conducted at a temperature between about 25° C. to about 70° C. (e.g., between about 35° C. to about 70° C., about 40° C. to about 70° C., about 50° C. to about 70° C., about 60° C. to about 70° C., about 25° C. to about 60° C., about 25° C. to about 50° C., about 25° C. to about 40° C., about 30° C. to about 60° C.) for a time period from about 5 to about 60 minutes (e.g., from about 5 to about 45 minutes, from about 5 to about 30 minutes, from about 5 to about 15 minutes, from about 5 to about 10 minutes, from about 10 to about 30 minutes, from about 15 to about 30 minutes, from about 20 to about 30 minutes, from about 10 to about 25 minutes, from about 10 to about 20 minutes).

In certain embodiments, subsequent coating layers (e.g., second or third layers) are applied to the base layer immediately following curing while the base layer is still at elevated temperature (i.e., above 25° C.). In other embodiments, the base layer fully cools to room temperature (i.e., 25° C.) prior to application of subsequent coating layers.

In certain embodiments, the first or base layer has a thickness in the range from about 0.01 mm to about 1.0 mm (e.g., from about 0.02 mm to about 1.0 mm, from about 0.05 mm to about 1.0 mm, from about 0.1 mm to about 1.0 mm, from about 0.2 mm to about 1.0 mm, from about 0.4 mm to about 1.0 mm, from about 0.6 mm to about 1.0 mm, from about 0.01 mm to about 0.8 mm, from about 0.01 mm to about 0.5 mm, from about 0.01 mm to about 0.2 mm, from about 0.01 mm to about 0.1 mm, from about 0.01 mm to about 0.08 mm, from about 0.01 mm to about 0.05 mm, from about 0.05 mm to about 0.1 mm).

In certain embodiments, the first or base layer has a thickness less than about 1.0 mm (e.g., less than about 0.8 mm, less than about 0.5 mm, less than about 0.4 mm, less than about 0.2 mm, less than about 0.1 mm, less than about 0.05 mm).

In certain embodiments, the second, or the third if present, or top layer has a thickness in the range from about 0.01 mm to about 1.0 mm (e.g., from about 0.02 mm to about 1.0 mm, from about 0.05 mm to about 1.0 mm, from about 0.1 mm to about 1.0 mm, from about 0.2 mm to about 1.0 mm, from about 0.4 mm to about 1.0 mm, from about 0.6 mm to about 1.0 mm, from about 0.01 mm to about 0.8 mm, from about 0.01 mm to about 0.5 mm, from about 0.01 mm to about 0.2 mm, from about 0.01 mm to about 0.1 mm, from about 0.01 mm to about 0.08 mm, from about 0.01 mm to about 0.05 mm, from about 0.05 mm to about 0.1 mm).

In certain embodiments, the second, or the third if present, or top layer has a thickness less than about 1.0 mm (e.g., less than about 0.8 mm, less than about 0.5 mm, less than about 0.4 mm, less than about 0.2 mm, less than about 0.1 mm, less than about 0.05 mm).

As discussed herein, in certain preferred embodiments, the coating application consists of applying a layer of the hydrophilic and latex polymer blend coating formulation over a latex base layer, which is applied to the latex product surface. In some embodiments, the sequential hydrophilic coating application and curing process may be repeated a plurality of times. For example, a hydrophilic and latex polymer coating is applied onto a latex substrate with a subsequent layer being the hydrophilic and latex polymer latex. In another embodiment, the subsequent hydrophilic and latex polymer is applied onto a hydrophilic and latex polymer coating blend that served as the first or base layer. In some embodiments, multiple coatings can be applied dependent on the desired properties to be achieved. Exemplary coating strategies are listed in Table 1.

TABLE 1

Coating layer order in various coating process embodiments

| | Coating Layer 1 | Coating Layer 2 | Coating Layer 3 |
|---|---|---|---|
| A | Latex | Hydrophilic and Latex Polymer blend coating formulation | |
| B | Hydrophilic and Latex Polymer coating formulation | Latex | |
| C | Latex | Hydrophilic and Latex Polymer coating formulation | Hydrophilic and Latex Polymer coating formulation |
| D | Hydrophilic and Latex Polymer coating formulation | Hydrophilic and Latex Polymer coating formulation | Latex |
| E | Latex | Latex | Hydrophilic and Latex Polymer coating formulation |
| F | Hydrophilic and Latex Polymer coating formulation | Latex | Latex |
| G | Hydrophilic and Latex Polymer coating formulation | Latex | Hydrophilic and Latex Polymer coating formulation |
| H | Latex | Hydrophilic and Latex Polymer coating formulation | Latex |

In yet another aspect, the invention generally relates to a condom manufactured by a method disclosed herein.

As disclosed herein, suitable additives may be added to assist in achieving one or more desired properties or enhancements in the compositions or products of the inventions.

In certain embodiments, the hydrophilic and latex polymer blend coating formulation, and the coated product, includes one or more antimicrobials such as antifungals, antibacterials, and metallic nanoparticles and/or microparticles that deter microbial growth. Examples of antifungal agents include, but are not limited to, Amphotericin B, lactic acid, sorbic acid, Clotrimazole, Ciclopirox, Carbol-Fushsin Econazole, Enilconazole, Fluconazole, Griseofulvin, Halogropin, Introconazole, Ketoconazole, Miconazole, Mafenide, Naftifine, Nystatin, Oxiconazole, Thiabendazole, Sulconazole, Tolnaftate, Undecylenic acid, Terbinafine, and Silver Sulfadiazine. Additionally, antibiotics and other antimicrobial agents can be selected from the group consisting of bacitracin; the cephalosporins (such as cefazolin, cefadroxil, cephalothin, cephalexin, ceftazidime, ceftriaxone, ceftizoxime, and meropenem); cycloserine; fosfomycin, the penicillins (such as amdinocillin, amoxicillin, ampicillin, azlocillin, benzathine penicillin G, bacamipicillin, carbenicillin, cyclacillin, cloxacillin, dicloxacillin, mezlocillin, methicillin, oxacillin, nafcillin, penicillin G, penicillin V, piperacillin, and ticarcillin); vancomycin; ristocetin; colistin; novobiocin; the polymyxins (such as colistin, colistimathate, and polymyxin B); the aminoglycosides (such as neomycin, amikacin, kanamycin, gentamicin, netilmicin, paromomycin, streptomycin, spectinomycin, and tobramycin), the tetracyclines (such as demeclocycline, do+-xycycline, minocycline, methacycline, and oxytetracycline); carbapenems (such as imipenem); monobactams (such as aztreonam); clindamycin; chloramphenicol; cycloheximide; fucidin; lincomycin; rifampicin; puromycin; other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim. Other antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; zinc-, copper-, or silver-based compounds, particles (micro- or nano-) and benzoic acid.

In certain embodiments, the hydrophilic and latex polymer blend coating formulation, and the coated product, includes one or more antivirals, antiretrovirals, or any like compounds that prevent the spread of viruses. Examples of antiviral agents can include, but are not limited to, adamantine antivirals, antiviral boosters, antiviral combinations, antiviral interferons, chemokine receptor antagonist, integrase strand transfer inhibitor, miscellaneous antivirals, neuraminidase inhibitors, NNRTIs, NS5A inhibitors, nucleoside reverse transcriptase inhibitors, protease inhibitors, and purine nucleosides. Other agents and drugs can also include Abacavir, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine.

In certain embodiments, the hydrophilic and latex polymer blend coating formulation, and the coated product, includes one or more vitamins, for example, Vitamins A, C, D, E, K and B, as well as thiamine (B1), riboflavin (B2), niacin (B3), pantothenic acid (B5), pyroxidine(B6), biotin (B7), folate (B9) and cobalamin (B12).

In certain embodiments, the hydrophilic and latex polymer blend coating formulation, and the coated product, includes one or more pigments or colorants, for example, C.I. Pigment Red 48:2 Permanent Carmine, C.I. Pigment Blue 15:2/Copper Phthalocyanine Blue, C.I. Pigment Green 7/Polychloro Copper phthalocyanine Green, C.I. Pigment Yellow 74 Azo Yellow.

In certain embodiments, the hydrophilic and latex polymer blend coating formulation, and the coated product, include other additives suitable for use with a condom product, such as one or more of plasticizers, accelerators, stabilizers, anticoagulants, preservatives, or other compounds can be added to the natural or synthetic latex solution to assist or accelerate the vulcanization process or to improve its mechanical properties. In some embodiments, these additives can include, but are not limited to, ammonia, proteins, nitrosamine, zinc chloride, zinc oxide, stearic acid, antidegradants, plasticizers, sulfur, peroxides, acetic acid, citric acid, formic acid, metallic oxides, potassium laurate, acetoxysilanes, urethane crosslinkers, polychloroprene, ethylene thiourea, or other equivalent accelerators, catalysis, or curatives. In another embodiment, more than one of these additives or compounds can be added into the latex solution.

The following examples are meant to be illustrative of the practice of the invention, and not limiting in any way.

EXAMPLES

Hydrophilic and Latex Polymer Mend Formulations and Coated Condoms

The hydrophilic and latex polymer blend formulation was studied by exploring different (1) hydrophilic polymer concentrations in water (e.g., ranging from 20 w/v % to 0.5 w/v %); (2) hydrophilic polymers (e.g., PEG, PVP, and PVA); (3) latex polymer solid content concentration in solution (e.g., from 40-60 w/v %); (4) solution ratios to blend the dissolved hydrophilic polymer in water and latex polymer suspension to produce the hydrophilic and latex polymer blend; and (5) viscosities of the hydrophilic and latex polymer blend and their effects on the homogeneity and thickness of the condom coating application.

Well-mixed solutions were used with the two components evenly distributed throughout the solution. Various formulations were used to coat latex substrates on glass slides (applied with heat at 60° C. to eliminate UV exposure) and were inspected to meet the following requirements: (1) have a slippery coated surface touch after rubbing samples back-and-forth 20 times with fingers and water; (2) maintain the elasticity and flexibility of natural rubber when stretched on an instron without breaking; and (3) hydrophilic and latex polymer blend coating did not delaminate, peel, or crack after rubbing and stretching.

Certain preferred hydrophilic and latex polymer blend formulations were identified to have an about 5% w/v polyvinylpyrrolidone (PVP) dissolved in water that was blended with an about 40 w/v % latex solution. The well-mixed hydrophilic and latex polymer blend coating formulation was reproducibly applied onto latex condoms using a dip-coating approach and is cured onto latex surfaces using heat at about 60° C. for about 15 minutes. This prototype resulted in a coating that was thin and flexible, possessed similar mechanical and physical properties as the latex, and had good adhesion properties onto latex substrates (e.g., no cracking, delamination, peeling).

TABLE 2

Latex blend coating formulations preparation with PEG, PVP, and PVA

| Hydrophilic polymer | Stock Solution (w/v %) | Hydrophilic and Latex Blend Ratio (liquid latex:hydrophilic polymer) | | | | |
|---|---|---|---|---|---|---|
| PEG | 20 | 1:1 | 2:1 | 1:2 | 5:1 | 1:5 |
|  | 10 | 1:1 | 2:1 | 1:2 | 5:1 | 1:5 |
|  | 5 | 1:1 | 2:1 | 1:2 | 5:1 | 1:5 |
|  | 1 | 1:1 | 2:1 | 1:2 | 5:1 | 1:5 |
| PVP | 20 | 1:1 | 2:1 | 1:2 | 5:1 | 1:5 |
|  | 10 | 1:1 | 2:1 | 1:2 | 5:1 | 1:5 |
|  | 5 | 1:1 | 2:1 | 1:2 | 5:1 | 1:5 |
|  | 1 | 1:1 | 2:1 | 1:2 | 5:1 | 1:5 |
| PVA | 20 | 1:1 | 2:1 | 1:2 | 5:1 | 1:5 |
|  | 10 | 1:1 | 2:1 | 1:2 | 51 | 1:5 |
|  | 5 | 1:1 | 2:1 | 1:2 | 5:1 | 1:5 |
|  | 1 | 1:1 | 2:1 | 1:2 | 5:1 | 1:5 |

Non-lubricated latex condoms were unrolled, washed with water, and patted dry to remove any starchy powder from the packaging. Latex condom strips (2×6 cm) were cut from the latex condoms and mounted on glass slides. 5 mL of latex blend coating formulations were prepared by mixing freshly purchased liquid latex (natural rubber) with stock solutions of polyvinyl pyrrolidone (PVP), poly(ethylene glycol) (PEG), or poly(vinyl alcohol) (PVA) in water. According to Table 2, each of the hydrophilic and latex polymer blend coating formulations were prepared by first dissolving the hydrophilic polymer in water at varying water to stock solution ratios, as measured in total weight to stock solution volume. This solution was then mixed with the latex suspension at varying latex-to-hydrophilic polymer solution ratios as noted in Table 2. A thin even layer of each solution was placed onto the latex strips which were immediately placed in an oven at about 60° C. to be dried for about 15 minutes. Samples were removed from the oven and allowed to cool to room temperature before assessing the coating.

Each of the hydrophilic and latex polymer blend coating formulation and respective coated latex samples were evaluated via touch with and without water by contact with dry skin and assessed according to the following parameters: (A) feasibility to obtain a well-mixed, viscous solution when mixed; (B) ability to maintain similar flexible properties as non-lubricated, uncoated latex condoms when stretched without water; (C) slippery and lubricous when wetted; and, finally (D) ability to maintain lubricity after about 20 rubs when wetted.

The degree of slipperiness and lubricity in parameter (C) was further evaluated subjectively in comparison to uncoated latex condom strips with the following ratings: (1) similar to plain latex, (2) slippery, and (3) very slippery.

Tables 3-5 summarize the assessments of the latex blend coating formulations and their resulting coatings on latex strips when prepared with PEG, PVP, and PVA, respectively. In view of the results presented in Table 3 for PEG formulations, none of the PEG formulations showed improved slipperiness, parameter (C), as compared to a conventional uncoated condom.

In view of the results presented in Table 4 for PVP formulations, the PVP formulations in the range of about 10.0 to about 12.5 w/v % with ratios of about 1:1, 2:1 and 1:2 as well as a PVP formulation of about 5.0 w/v % with a ratio about 1:1 are each demonstrated to have (A) feasibility to obtain a well-mixed, viscous solution when mixed; (B) ability to maintain similar flexible properties as non-lubricated, uncoated latex condoms when stretched without water; (C) very slippery or slippery and lubricous when wetted as compared to a conventional uncoated condom as according to the following rating system: (1) similar to plain latex; (2) slippery; and (3) very slippery; and, (D) ability to maintain lubricity after about 20 rubs when wetted.

In view of Table 5 for PVA formulations, the PVA formulation of about 5.0 w/v % with a ratio of about 1:5 is demonstrated to have (A) feasibility to obtain a well-mixed, viscous solution when mixed; (B) ability to maintain similar flexible properties as non-lubricated, uncoated latex condoms when stretched without water; (C) very slippery or slippery and lubricous when wetted as compared to a conventional uncoated condom; and, (D) ability to maintain lubricity after about 20 rubs when wetted.

Accordingly in view of Tables 3-5, that the preferred coating resulted from a hydrophilic and latex polymer blend coating formulation prepared with about 10 w/v % to about 12 w/v % PVP in water mixed with a liquid latex solution at about 1:1 or 1:2 ratio. A preferred hydrophilic and latex polymer blend formulation has a final PVP concentration of about 2 w/v % to about 8 w/v % as noted in Table 5.

Identifying the appropriate hydrophilic polymer, as well as optimizing the concentration ranges and method for formulation preparation to develop the final solution was critical to develop a robust, flexible, and elastic cured substrate coating that possessed long-lasting lubricating surface with water. PVP was particularity selected since both PEG and PVA did not offer the desired lubricating properties on the latex surface even at high concentrations up to 20 w/v % as their slippery properties did not consistently last up till 20 rubs using fingers in the presence of water. PVA polymers are known to be rigid which in return reduces the flexibility of the latex substrate, thus inhibiting its ability to be stretched and elastic. When varying ratios of PVP in water was mixed with the liquid latex suspension, low concentrations of PVP in the final solution (e.g. <2 w/v %) resulted in limited durability of the coating's lubricating properties due to insufficient PVP present in the final cured substrate. Yet, with higher concentrations of PYP (e.g, >8 w/v %) in the final concentration solution in relation to liquid latex, this interfered with the ability for latex to cure to form a durable flexible substrate while inhibiting the formation an interpenetrating network with the PVP. As a result, the cured substrates were brittle and easily broke when bent and stretched. Similar observations were also noted with solutions containing low concentrations of latex in solution (e.g. >20 w/v %). Higher concentrations of latex in the final formulation (e.g. >30 w/v %) also inhibit the lubricating properties of PVP in solution due to the large concentration and presence of latex in the solution, which masked the PVP within the interpenetrating network.

TABLE 3

Assessment of latex blend coating formulations and resulting coating with PEG

| Latex Blend Formulation with PEG | | A | B | C 1 | C 2 | C 3 | D |
|---|---|---|---|---|---|---|---|
| 20 w/v % | 1:1 | X | X | X | | | |
| | 2:1 | X | X | X | | | |
| | 1:2 | | X | X | | | |
| | 5:1 | X | X | X | | | |
| | 1:5 | | X | X | | | |

TABLE 3-continued

Assessment of latex blend coating formulations and resulting coating with PEG

| Latex Blend Formulation with PEG | | A | B | C 1 | C 2 | C 3 | D |
|---|---|---|---|---|---|---|---|
| 10 w/v % | 1:1 | X | X | X | | | |
| | 2:1 | X | X | X | | | |
| | 1:2 | | X | X | | | |
| | 5:1 | X | X | X | | | |
| | 1:5 | | X | X | | | |
| 5 w/v % | 1:1 | X | X | X | | | |
| | 2:1 | X | X | X | | | |
| | 1:2 | | X | X | | | |
| | 5:1 | X | X | X | | | |
| | 1:5 | | X | X | | | |
| 1 w/v % | 1:1 | | X | X | | | |
| | 2:1 | | X | X | | | |
| | 1:2 | | X | X | | | |
| | 5:1 | X | X | X | | | |
| | 1:5 | | X | X | | | |

TABLE 4

Assessment of hydrophilic and latex polymer blend coating formulations and resulting coating with PVP

| Latex Blend Formulation with PVP | | A | B | C 1 | C 2 | C 3 | D |
|---|---|---|---|---|---|---|---|
| 20 w/v % | 1:1 | | | | | X | X |
| | 2:1 | | | | | X | X |
| | 1:2 | | | | | X | X |
| | 5:1 | X | X | X | | | |
| | 1:5 | | X | X | | | |
| 15 w/v % | 1:1 | X | | | X | | |
| | 2:1 | X | | | X | | |
| | 1:2 | X | | | X | | |
| | 3:1 | X | | X | | | |
| | 1:3 | X | | X | | | |
| 12.5 w/v % | 1:1 | X | X | | | X | X |
| | 2:1 | X | X | | | X | X |
| | 1:2 | X | X | | | X | X |
| | 3:1 | X | X | X | | | |
| | 1:3 | X | X | | X | | |
| 10 w/v % | 1:1 | X | X | | | X | X |
| | 2:1 | X | X | | | X | X |
| | 1:2 | X | X | | | X | X |
| | 3:1 | X | | | X | | |
| | 1:3 | X | | | X | | |
| | 5:1 | X | X | X | | | |
| | 1:5 | | X | X | | | |
| 7.5 w/v % | 1:1 | X | X | | X | | |
| | 2:1 | X | X | | X | | |
| | 1:2 | X | X | | X | | |
| | 3:1 | X | X | X | | | |
| | 1:3 | X | X | X | | | |
| 5 w/v % | 1:1 | X | X | | X | | X |
| | 2:1 | X | X | | X | | |
| | 1:2 | X | X | | X | | |
| | 3:1 | X | X | X | | | |
| | 1:3 | X | X | X | | | |
| | 5:1 | X | X | X | | | |
| | 1:5 | | X | X | | | |

TABLE 4-continued

Assessment of hydrophilic and latex polymer blend coating formulations and resulting coating with PVP

| Latex Blend Formulation with PVP | | Assessment Parameters of Coating on Latex Strips | | | | | |
|---|---|---|---|---|---|---|---|
| | | A | B | C | | | D |
| | | | | 1 | 2 | 3 | |
| 1 w/v % | 1:1 | X | X | X | | | |
| | 2:1 | X | X | X | | | |
| | 1:2 | X | X | X | | | |
| | 5:1 | X | X | X | | | |
| | 1:5 | | X | X | | | |

TABLE 5

Assessment of hydrophilic and latex polymer blend coating formulations and resulting coating with PVA

| Latex Blend Formulation with PVA | | Assessment Parameters of Coating on Latex Strips | | | | | |
|---|---|---|---|---|---|---|---|
| | | A | B | C | | | D |
| | | | | 1 | 2 | 3 | |
| 20 w/v % | 1:1 | | | X | | | |
| | 2:1 | | | X | | | |
| | 1:2 | | | X | | | |
| | 5:1 | | | X | | | |
| | 1:5 | X | X | X | | | |
| 10 w/v % | 1:1 | | X | X | | | |
| | 2:1 | | X | X | | | |
| | 1:2 | | X | X | | | |
| | 5:1 | X | | X | | | |
| | 1:5 | | X | | X | | X |
| 5 w/v % | 1:1 | X | X | X | | | X |
| | 2:1 | X | X | X | | | X |
| | 1:2 | X | X | X | | | X |
| | 5:1 | X | X | X | | | X |
| | 1:5 | X | X | | X | | X |
| 1 w/v % | 1:1 | X | X | X | | | X |
| | 2:1 | X | X | X | | | X |
| | 1:2 | X | X | X | | | X |
| | 5:1 | X | X | X | | | X |
| | 1:5 | X | X | X | | | X |

The physical and lubrication properties of the hydrophilic and latex polymer blend-coated condoms were analyzed in accordance to parameters listed in Table 6. The results revealed that (1) the hydrophilic and latex polymer blend formulation was reproducibly scalable (e.g., on a liter and multi-kilo-liter scale) with a quicker dip-coating application onto latex substrates, (2) hydrophilic and latex polymer blend coating resulted in improved adhesion with heat (no peeling, cracking, or delamination noted when stretched) to the latex without damaging the material (tensile testing), (3) hydrophilic and latex polymer blend coating had improved mechanical properties and flexibility when stretched with (out) water, (4) the hydrophilic and latex polymer blend-coated condoms had long-lasting lubrication durability in the presence of water through friction studies with a male masturbator. The hydrophilic and latex polymer blend coating was slippery with water and aqueous solutions via touch, thin and homogenous (measured with a digital micrometer/SEM and AFM studies), non-cytotoxic, and flexible. The hydrophilic and latex polymer blend-coated condoms also maintained consistently lower frictional forces compared to commercial lubricants and standard lubricated condoms.

TABLE 6

Tested parameters for hydrophilic and latex polymer blend-coated condoms

| Test/Analysis | Parameters |
|---|---|
| Coating Thickness of HGCoat on latex | 1.0-0.6 mm |
| Visual inspection | Presence of a homogenous surface/coating application reproducibility between units and batches |
| Coating Durability Studies #1 | Coating remains on surface after rubbing with fingers after 10 times with water |
| Coating Durability Studies #2 | Coating present after 20 insertions into masturbator |
| Airburst testing | N = 3; must hold 18 L of air at 1 kPa/conducted under ISO standards |

Coating Process for Large-Scale GMP Manufacturing of Hydrophilic and Latex Polymer Blend-Coated Condoms The followings were studied: (1) the large scale production of the hydrophilic and latex polymer blend formulation (e.g., on a multi-liter scale), (2) adaption of dip-coating processes and equipment for coating application under GMP standards, (3) automation of the dip-coating application process onto latex condoms, (4) various dip-coating speed ranges and their effects on the coating thickness and application homogeneity, and (5) reproducibility and uniformity of the coating application on condoms through different units and batches at varying speed.

The formulation prototype prepared on a 500 mL scale for laboratory assessments and on a 2 to 3 L scale under GMP standards were reproducible and consistent between 3 different batches. FIG. 2 depicts minor adjustments made to the dip-coating instrumentation to translate manual dipping the hydrophilic and latex polymer blend coating application procedure (FIG. 1C) to an automatic process. The hydrophilic and latex polymer blend-coated condoms prepared with this setup were consistent between the units and batches. In conclusion, these results demonstrated the feasibly for the hydrophilic and latex polymer blend formulation to be scalable in the large-scale manufacturing.

The preferred dip-coating speed range was identified for forming the first base layer and the second hydrophilic and latex polymer blend layer to generate a homogenous and thin coating. Small batches of the hydrophilic and latex polymer blend-coated condoms, ranging from 2-26 units per batch, were produced and analyzed based on parameters in Table 6.

Figure 2:
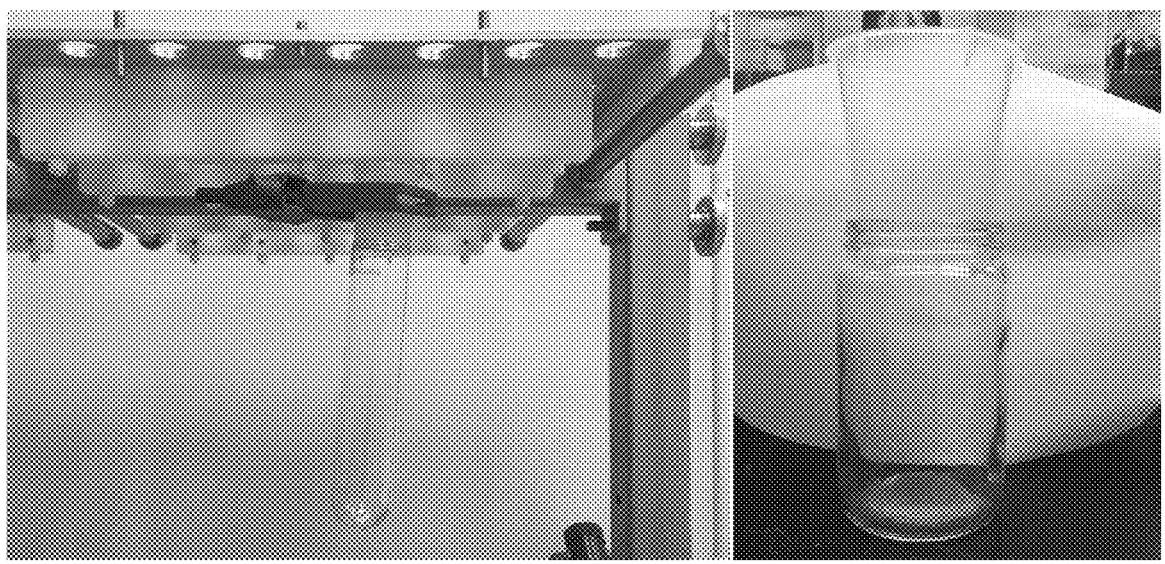
FIG. 2. Modifications and fixtures made to accommodate the hydrophilic and latex polymer blend coating application on latex condoms to their standard dip-coating equipment under GMP-like conditions. (Left) Schematic of one dip-coating fixture on their automatic instrument; (Right) the hydrophilic and latex polymer blend formulation was prepared in container.

As demonstrated in FIG. 1C, an 18 mm glass mandrel was placed into the latex solution to form the first base coat layer using dip-coating speeds ranging from about 0.1 mL/min to about 0.4 mL/min. Once removed from the barrel, the glass mandrel was held over the solution to allow excess material to drip off for about 5 seconds while observing an even layer of latex solution on the mandrel. If an uneven layer was noted, the dip was repeated. The sample was cured in an oven at about 60° C. for about 10 minutes and then immediately dipped into a second barrel with the hydrophilic and latex polymer blend formulation at dip-coating speeds from about 0.2 mL/min to about 1.0 mL/min. Similarly, once the glass mandrel was removed, excess material dripped off for 5 seconds while examining an even coating on the latex surface. After heat curing the sample at about 60° C. for about 15 minutes, the sample cooled to room temperature, covered in alumni foil, and packaged in an airtight bag for further assessment. Details regarding the number of trial runs and dip-coating speed rates investigated are summarized in Table 7.

TABLE 7

Results of Trial Batches with Varying Dipping Speeds

| Batch run | No. of Condom Units | Dipping Speeds (mL/min) Base Coat | Dipping Speeds (mL/min) Top Coat | Visual Inspection Uniformity between batches | Visual Inspection Even coating on each unit | Slippery w/ water by touch and rubbing | Durability Studies[W] | Airburst Testing* | Thickness Measurements* (mm) Near Opening | Thickness Measurements* (mm) Middle | Thickness Measurements* (mm) Near Tip |
|---|---|---|---|---|---|---|---|---|---|---|---|
| 1 | 6 | 0.1 | 0.2 | Yes | Yes | Yes | Yes | Pass | 1.01 | 1.03 | 1.21 |
| 2 | 12 | 0.1 | 0.2 | Yes | Yes | Yes | Yes | Fail | 0.47 | 0.52 | 1.02 |
| 3 | 26 | 0.1 | 0.2 | Yes | Yes | Yes | Yes | Fail | 1.05 | 0.84 | 0.78 |
| 4 | 12 | 0.2 | 0.2 | Yes | Yes | Yes | Yes | Fail | 0.41 | 0.54 | 0.98 |
| 5 | 6 | 0.2 | 0.4 | Yes | Yes | Yes | Yes | Fail | 0.56 | 0.72 | 1.34 |
| 6 | 12 | 0.2 | 0.4 | Yes | Yes | Yes | Yes | Fail | 0.70 | 0.57 | 0.69 |
| 7 | 12 | 0.3 | 0.6 | Yes | Yes | Yes | Yes | Pass | 0.60 | 1.03 | 0.60 |
| 8 | 6 | 0.4 | 1.0 | Yes | Yes | Yes | Yes | Pass | 0.60 | 0.68 | 1.04 |
| 9 | 12 | 0.4 | 1.0 | Yes | Yes | Yes | Yes | Pass | 0.80 | 0.56 | 1.04 |

*Studies were done in accordance to requirements and standards stated under ISO 4074
Studies were conducted at n = 3 that were randomly selected in the batch produced; measurements shown are averages
[W]coating present after 20 insertions into masturbator with water A visual inspection of all samples was performed for uniformity between units and batches to ensure an even homogenous coating on the surface. Samples were wetted with water and rubbed with fingers to validate the lubricating properties of the coating. The coating durability was also tested by inserting 3 randomly selected samples per batch into the male masturbator 20 times with about 1.0 mL of water to ensure the coating remained present on the surface.

Thickness measurements using a digital micrometer on 3 selected units per batch (i.e. body, reservoir tip, base) were performed in accordance to ISO 4074. Three samples were sent to Akron Rubber Development Laboratory (Akron, Ohio) for airburst testing to ensure condoms could hold a minimum of 18 L of air at 1 kPa as stated under the ISO requirements. The results are summarized in Table 7.

The studies indicated that a preferred dip-coating speeds of about 0.3 mL/min to about 0.4 mL/min for the base layer and about 0.6 mL/min to about 1.0 mL/min for the second or top coat. The hydrophilic and latex polymer blend-coated condoms prepared at these speed ranges have met the parameters in Table 7 and were used for the following characterization studies.

Through frictional studies using a male masturbator, the hydrophilic and latex polymer blend-coated condoms showed improved durability and longer-lasting lubrication properties when compared to commercially available lubricants and personal lubrication products. Cytotoxicity of the hydrophilic and latex polymer blend-coated condoms were assessed using an epithetical fibroblast cell line in accordance to ISO 10993, which showed coated latex samples to have minimized cytotoxicity compared to non-coated latex samples.

Figure 3:
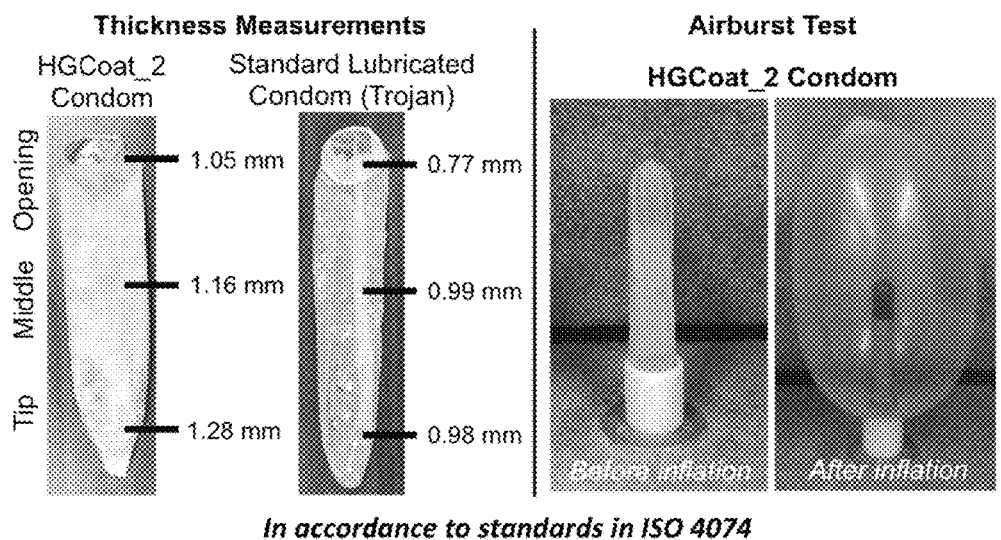
FIG. 3. Hydrophilic and latex polymer blend-coated condoms showed similar thickness when compared to a standard lubricated condom, which were measured using a digital micrometer as according to ISO 4074. (Right) Hydrophilic and latex polymer blend-coated condoms can withstand a minimum of 18 L and 1 kPa of air in airburst testing.

Mechanical testing of the hydrophilic and latex polymer blend-coated condoms were performed at. Akron Rubber Development Laboratory (Akron, Ohio) in accordance to ISO 4074, To test for holes, water leak tests were conducted by filling the hydrophilic and latex polymer blend-coated condoms with 300 mL of water, tying the opening, and manually hand-rolling condoms on color absorbent paper with slight pressure. Airburst testing was performed by filling condoms with a minimum of 18 L of air at 1 kPa (FIG. 3). Dimensional analyses were conducted by measuring the length of the condom using a ruler while the thickness of the condom using a standard digital micrometer near the opening, middle, and tip of the condom (FIG. 3). To ensure the coating did not weaken the latex, tensile testing was conducted with strips sectioned from the condom and were stretched at a rate of 500 mm/min. Commercially available lubricated condoms were included in the studies as controls.

The hydrophilic and latex polymer blend-coated condoms prepared using dip-coating speeds of about 0.3 mL/min to about 0.4 mL/min (base layer) and about 0.6 mL/min to about 1.0 mL/min (second or top coat) met requirements under ISO airburst and water-leak testing (Table 7). Tensile testing of the hydrophilic and latex polymer blend-coated condoms revealed similar results compared Trojan, Durex, and Lifestyles standard lubricated condoms, indicating that the hydrophilic and latex polymer blend coating did not weaken the latex material. Dimensional analysis data indicated condoms to be comparable in length and thickness to commercially available condoms (FIG. 3).

To achieve uniform thickness for the hydrophilic and latex polymer blend coating condoms in GMP manufacturing, glass mandrels can be simultaneously dipped and rotated into the glass barrel which are immediately removed and flipped to create a homogenous and even layer of the latex solutions on the glass mandrels.

Lubricity of the Hydrophilic and Latex Polymer Blend-Coated Condoms

Studies were performed regarding the minimal amount of water needed to lubricate the hydrophilic and latex polymer blend-coated condom surface, as well as the effects of water-based lubricants (KY liquid). For a fully unrolled hydrophilic and latex polymer blend-coated condom (standard 16 mm in length; 4 mm in diameter), it was determined that a minimum amount of 0.50 mL of water was needed to lubricate the entire coated condom surface. Lower amounts of water (e.g., 0.25 mL) only partially wetted the condom surface whereas >0.50 mL of water (e.g., 0.75 mL and 1.0 mL) did not attribute any additional lubricating properties or enhanced the coating slipperiness. Studies were repeated using KY Liquid and KY Jelly to understand whether the viscosity of these water-based personal lubricants affected the lubricating properties of the hydrophilic and latex polymer blend coating.

It was noted that about 1.0 mL of KY liquid was required to wet the entire surface of the coating due to its higher viscosity compared to water, making it more challenging to be evenly distribute on the condom surface. When comparing the slipperiness between the hydrophilic and latex polymer blend-coated condoms with about 0.5 mL of KY Liquid compared to non-lubricated condoms with about 0.5 mL of KY liquid via touch, similar slipperiness and lubricating properties after 10-15 rubs were found. The slipperiness from the non-lubricated condom with KY liquid began to wear away after 15 rubs, resulting in higher frictional forces, whereas the hydrophilic and latex polymer blend-coated condom with KY Liquid maintained similar slipperiness even up to about 40-50 rubs. We reasoned the aqueous properties of KY liquid could activate the HGcoat_2 similarly to water since no differences in slipperiness was observed between lubricating the condom with water or KY liquid. Further frictional studies and investigations were pursued using a male masturbator in addition to analyzing the effects of silicone-based personal lubricants, which is described as followed.

Figure 4:
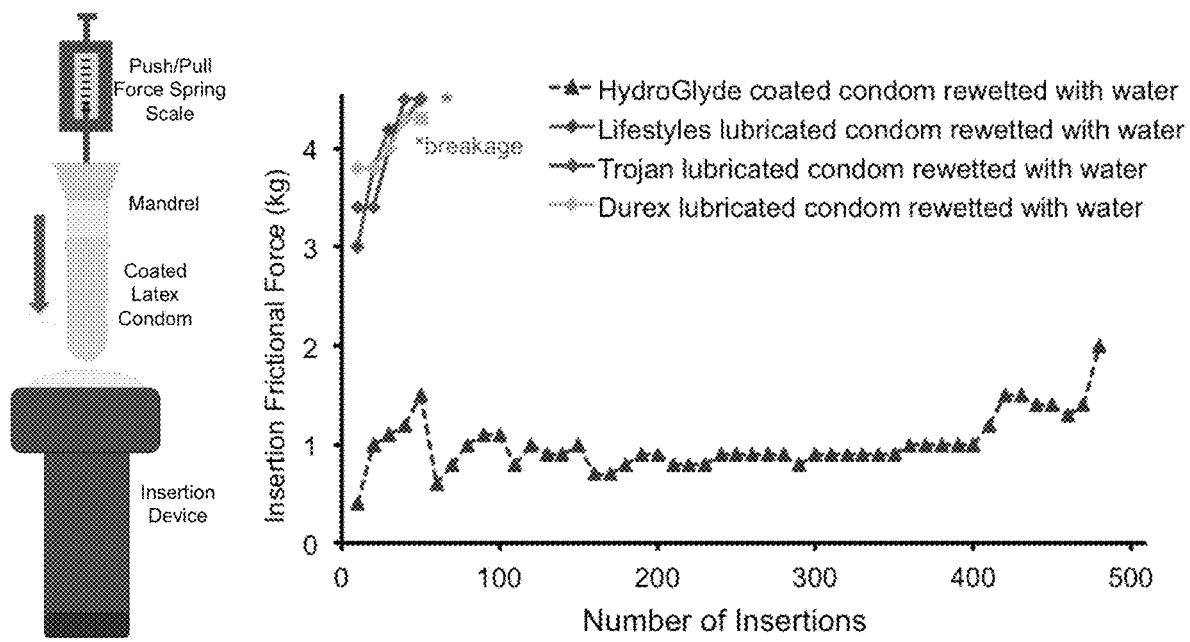
FIG. 4. Insertion apparatus using male masturbator for friction studies. (Right) Coating durability study of hydrophilic and latex polymer blend-coated condoms in comparison to Lifestyles, Durex, and Trojan lubricated condoms in the presence of water. Hydrophilic and latex polymer blend-coated condoms showed consistently low frictional forces even up to 500 insertions (blue) whereas all commercially available silicone-lubricated condoms broke even before 100 insertions.

To compare the hydrophilic and latex polymer blend coating lubrication durability to commercially available personal lubricants and lubricated condoms, a male masturbator (Fleshlight) was used as an insertion device. Condoms were placed on a glass mandrel attached to a push/pull force spring scale where frictional forces were recorded after every 10 insertions (FIG. 4). All studies were conducted with 500 insertions into the device with 0.5 mL of water added after every 50 insertions. Studies were terminated when condoms broke.

The lubricating properties and coating durability of the hydrophilic and latex polymer blend coating were compared to standard Durex, Lifestyles, and Trojan silicone-lubricated condoms. As a control, a non-lubricated condom with about 0.5 mL of water broke within about 10 insertions due to high frictional forces between the latex and device interface (FIG. 5; Grey Triangle (1)). As seen in FIG. 4., all three silicone-lubricated condoms (purple, red, orange) showed increasing frictional forces and broke before 100 insertions. Contrastingly, HGCoat_2 condoms (blue) maintained consistently low frictional forces into the device even up to 500 insertions. These results indicate that the hydrophilic and latex polymer blend-coated condoms offer longer-lasting condom lubricity compared to commercially available silicone-lubricated condoms.

Figure 5:
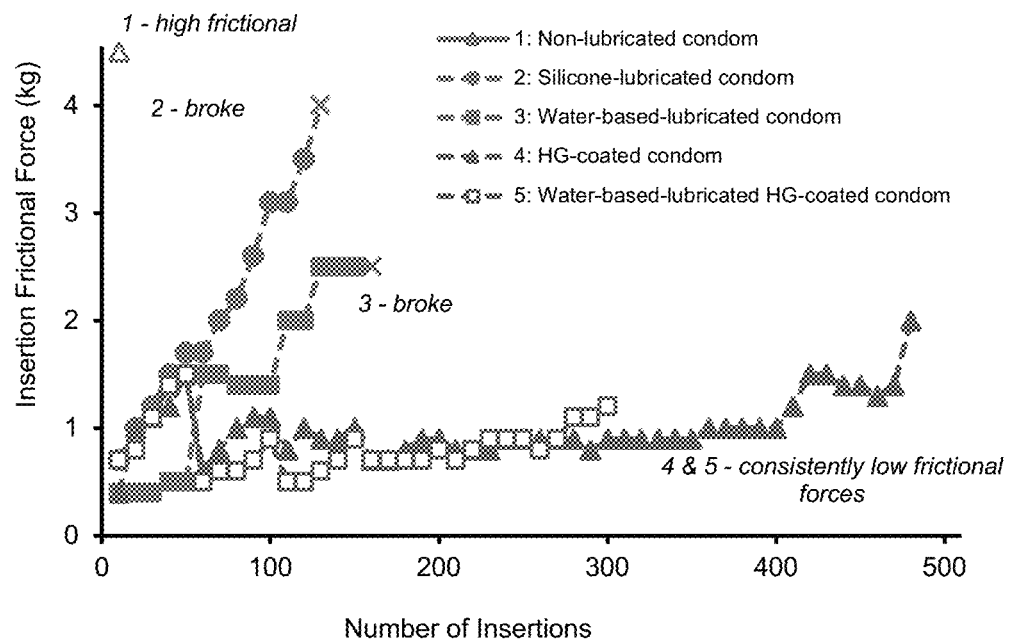
FIG. 5. Coating durability study of hydrophilic and latex polymer blend-coated condoms (green) to non-lubricated condoms (grey) with 0.5 mL of water-based personal lubricant, 0.5 mL of silicone-based personal lubricant, 0.5 mL of water.

Next, studies were conducted comparing the performance of the hydrophilic and latex polymer blend-coated condoms (green) to non-lubricated (grey) condoms with about 0.5 mL of a silicone lubricant (Astroglide), water-based lubricant (KY Liquid), and water. Non-lubricated condoms with silicone-lubricant (FIG. 5; labeled "silicone-lubricated condom") broke after 120 insertions while non-lubricated condoms with water-lubricant also broke after 170 insertions (FIG. 5; labeled "Weer-based-lubricated condom"). It was reasoned that the addition of water diluted these lubricants on the condom surface, which similarly occurs to personal lubricants under physiological conditions when exposed to the bodily fluids. Even higher frictional forces were measured when repeating studies without rewetting samples after every 50 insertions, as expected. In contrast, the hydrophilic and latex polymer blend-coated condoms (FIG. 5; labeled "Water-based-lubricated HG-coated condom"; green boxes) lubricated with 0.5 mL KY liquid could maintain low frictional forces similarly to the hydrophilic and latex polymer blend-coated condoms lubricated with water (FIG. 5; labeled "HG-coated condom"; green). Both demonstrated improved performance and its ability to offer longer-lasting condom lubricity. When repeating the study without rewetting the hydrophilic and latex polymer blend-coated condom after every 50 insertions, its performance was comparable to that of silicone-lubricated condoms. Additionally, it was noted that adding silicone-lubricant to the hydrophilic and latex polymer blend-coated condoms resulted in a similar lubricating properties and performance to commercially available silicone-lubricated condoms and non-lubricated condoms supplemented with a silicone personal lubricant.

Figure 6:
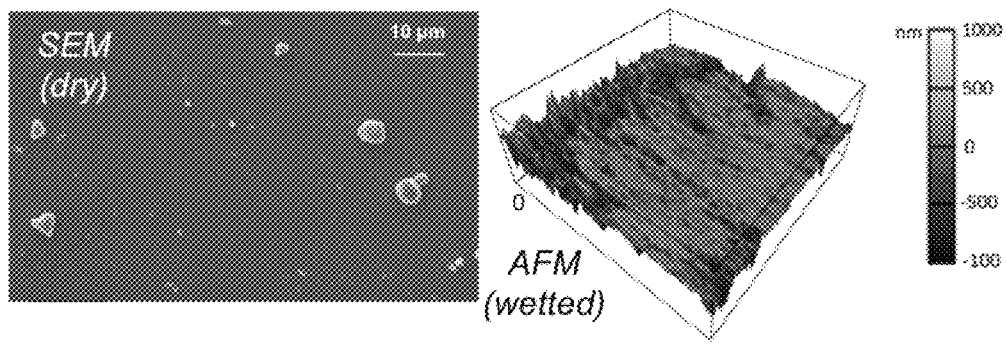
FIG. 6. Scanning electron microscopy (SEM) images (Left) at 10 μm resolution and Atomic Force Microscopy (AFM) images (Right) of (A.) non-coated and (B.) hydrophilic and latex polymer blend-coated latex surfaces.
Figure 6:
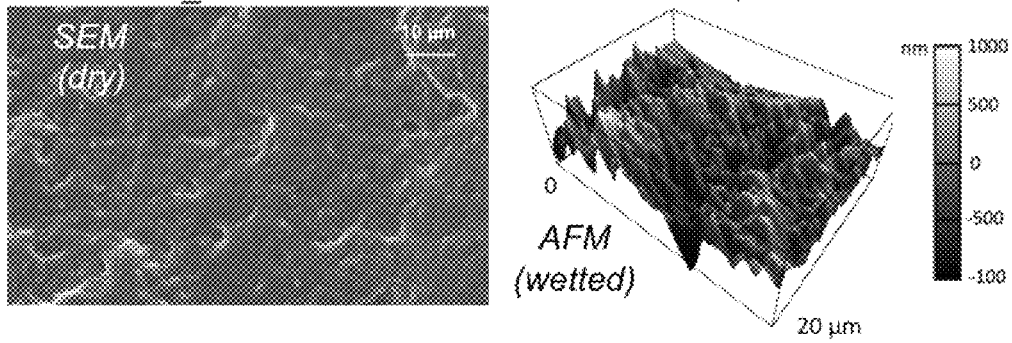

As noted in FIG. 6, SEM images of non-coated latex samples (FIG. 6A) depict a smooth surface while the HGCoat_2 coating on the latex was observed to result in a slightly rougher surface (FIG. 6B). This observation was confirmed via. AFM images when samples were imaged dry and with water. When imaging the surface via SEM through different parts of one condom and between different condoms, even coatings were noted, indicating the consistently and reproducibility within the hydrophilic and latex polymer blend coating. After rubbing the hydrophilic and latex polymer blend coating samples several times with water, the coating still remained on the surface.

These results demonstrated that the hydrophilic and latex polymer blend-coated condoms offer durable and longer-lasting condom lubricity compared to commercially available personal lubricants when in the presence of minimal water or aqueous fluids.

The Hydrophilic and Latex Polymer Blend Coatings are Non-Cytotoxic

To determine whether the hydrophilic and latex polymer blend coating had cytotoxic leachables, a standard cytotoxicity assay was conducted using a fibroblast cell line (L cell, L-929; ATTC CCL-1) in accordance with ISO 10993-5 (Microchem Laboratory; Round Rock, Tex.). In summary, the cell line was cultured in 24-well trays. Positive and negative controls were prepared in addition to the hydrophilic and latex polymer blend-coated and non-coated latex test samples (n=4), which were all sterilized by autoclaving. All samples were directly exposed and were in contact with the cell monolayer for 24 hours at 37° C. After incubation, test samples were removed and aliquots from the media were placed in culture vessels afterwards, which were cultured for another 24 hours. Cells were analyzed to evaluate any changes in the morphology, cell lysis, or destruction of the monolayer and were graded on a 0-4 scale correlating to no cytotoxicity (0; negative control) to severe cytotoxicity (4; positive control).

Since latex is cytotoxic due to its hydrophobic and fouling surface properties, the non-coated latex control and positive control both rated 4, correlating to severe cytotoxicity. The hydrophilic and latex polymer blend-coated samples were graded with a 2, correlating to mild cytotoxicity in respect to the controls, implying the hydrophilic and latex polymer blend coating reduces the cytotoxicity of the surface compared to non-coated latex.

Packaging Strategies with Rolled-Up Hydrophilic and Latex Polymer Blend-Coated Condoms In the standard GMP manufacturing process, condoms are typically powdered lightly (to ensure the latex does not stick to itself when packaged), rolled up, and packaged with ~0.5 mL of silicone lubricant prior to sealing the final product in an airtight foil. Various packaging strategies with and without lubricants and powders or dusting agents to ensure packaging hydrophilic and latex polymer blend-coated condoms are compatible under these conditions.

Figure 7:
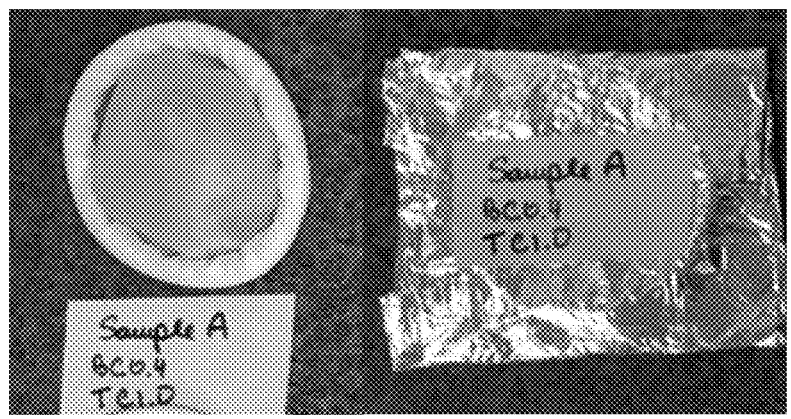
FIG. 7. Example of a hydrophilic and latex polymer blend-coated condom with baby powder that has been rolled-up (left) and packaged in foiled (right).

Samples were rolled up from glass mandrels after adding different powders or dusting agents (e.g., corn starch, baby power/talc) or personal lubricants (e.g., silicone- or water-based products) to the surface. Six packaging samples investigated which included (1) no lubricant/powers (control); (2) 0.5 mL (standard) of silicone lubricant; (3) 0.5 mL of water-based lubricant; (4) water; (5) corn starch to the surface; and, (6) baby powder to the surface. Also explored was lubricating and applying powders or dusting agents to the inside and/or outside of condoms. All test samples (n=3) were wrapped in foil and packaged in an airtight bag at room temperature. FIG. 7 shows an example of a rolled up and packaged condom with baby powder. After 7 days, to analyzing the samples, condoms were unrolled and confirmed the lubricant/powders or dusting agents remained on the condom surface after unrolling via visual inspection. Sample were wetted with 0.5 mL of water and rubbed with fingers to determine whether the lubricants, powders, or dusting agents altered the coating's lubricating properties.

As expected, condoms packaged without lubricants or powders (control) were challenging to unroll as the latex adhered to itself. Samples packaged with powders, both cornstarch and baby powder on the inside and outside of condoms, were easily unrolled and the hydrophilic and latex polymer blend-coated surface was slippery with water. Samples packaged with water or the water-based lubricant resulted in sticky surfaces when the condom was unrolled, suggesting these lubricants are incompatible for condom packaging. This observation was consistent with current condom packaging standards since water-based lubricants are typically avoided for packaging, which can promote bacterial growth.

Silicon-lubricated hydrophilic and latex polymer blend-coated condoms were challenging to roll-up for packaging due to the slippery nature of the lubricant. After unrolling the samples, the silicone lubricant was visually present on the surface. However when wetting the hydrophilic and latex polymer blend-coated surface with water, it was observed a minor reduction in lubricating properties of the hydrophilic and latex polymer blend coating. The hydrophobic silicone lubricant appeared to have prevented water and water-based lubricants to be in contact with the condom surface. After rubbing the silicone lubricant off the condom with clean fingers to resemble the silicone lubricant wearing away during intercourse, the coating was fully lubricated and slippery with water, making this a viable option for packaging. Additionally, we explored packing hydrophilic and latex polymer blend-coated condoms with powdered on the surface prior to the addition of silicon lubricant similarly to the standard packaging processes, which resulted in similar findings.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. An aqueous composition, comprising:
   a hydrophilic polymer selected from poly(vinyl pyrrolidone) (PVP), poly(ethylene glycol) (PEG), and poly (vinyl alcohol) (PVA);
   a suspension of latex polymer microparticles; and
   one or more of vulcanizing or accelerating agents, wherein
   the hydrophilic polymer has a mean molecular weight in the range from about 100 kDa to about 10,000 kDa and is present in the composition at a concentration from about 2 w/v % to about 7 w/v %;

the latex polymer microparticles are present in the composition at a concentration from about 35 w/v % to about 65 w/v %;

a viscosity in the range from about 10 cP to about $10^{10}$ cP; and the weight ratio of the hydrophilic polymer to the latex polymer microparticles is in the range from about 1:1 to about 1:3.

2. The composition of claim 1, being an evenly mixed and stable suspension.

3. A composition formed by mixing:

a first aqueous solution of a hydrophilic polymer selected from poly(vinyl pyrrolidone) (PVP), poly(ethylene glycol) (PEG), and poly(vinyl alcohol) (PVA) with a concentration in the range from about 1 w/v % to about 20 w/v %; and a second aqueous suspension of latex polymer microparticles with a concentration in the range from about 35 w/v % to about 70 w/v %; and wherein the hydrophilic polymer has a mean molecular weight in the range from about 100 kDa to about 10,000 kDa; and the volume ratio of the first aqueous solution to the second aqueous suspension is in the range from about 1:1 to about 1:3, wherein the hydrophilic polymer is present in the composition at a concentration from about 2 w/v % to about 7 w/v %;

the latex polymer microparticles are present in the composition at a concentration from about 35 w/v % to about 65 w/v %.

4. The composition of claim 3, having the hydrophilic polymer at a concentration from about 2 w/v % to about 7 w/v % and the latex polymer microparticles at a concentration from about 20 w/v % to about 60 w/v %.

5. The composition of claim 1, wherein the hydrophilic polymer comprises PVP.

6. The composition of claim 5, wherein the hydrophilic polymer comprises a second hydrophilic polymer.

7. The composition of claim 3, further comprising one or more of vulcanizing agents or accelerating agents.

8. The composition of claim 7, wherein the one or more of vulcanizing agents or the one or more of accelerating agents are present in the first aqueous solution a hydrophilic polymer.

9. The composition of claim 7, wherein the one or more of vulcanizing agents or the one or more of accelerating agents are present in the second aqueous suspension of latex polymer microparticles.

10. The composition of claim 9, wherein the vulcanizing agents are selected from the group consisting of: diisopropyl xanthogen polysulfide, sulfur, and ammonia and the accelerating agents are selected from the group consisting of: zinc-N-diethyl-dithio-carbomate, zinc-N-dibutyl-dithio-carbomate, and ammonia.

11. The composition of claim 1, further comprising one or more of antimicrobials, antivirals, antifungals, vitamins, colors, or antibiotics.

12. The composition of claim 1, wherein the latex polymer is natural latex.

13. The composition of claim 1, wherein the latex polymer is synthetic latex.

14. The composition of claim 1, wherein the synthetic rubber latex is synthetized from isoprene, nitrile, butadiene, styrene-butadiene, chloroprene, isobutylene, or co-polymers thereof.

15. A cured material formed by heating the composition of claim 1 for a time sufficient to form interpenetrating polymer networks of crosslinked hydrophilic polymer and latex polymer.

16. The cured material of claim 15, wherein the material is a coating forming a surface of a product.

17. The cured material of claim 16, wherein the product is selected from the group consisting: a condom, a sex toy, a surgical device, a medical implant, or a glove.

18. The cured material of claim 17, wherein the cured material is less cytotoxic compared to non-coated latex materials alone.

* * * * *